United States Patent [19]
Brenman

[11] Patent Number: 6,147,086
[45] Date of Patent: Nov. 14, 2000

[54] METHOD EMPLOYING IMIQUIMOD CREAM FOR TREATMENT OF TOPICAL SARCOIDOSIS ON EQUINE

[76] Inventor: Steven A. Brenman, 4960 S. Lafayette La., Cherry Hills, Colo. 80110

[21] Appl. No.: 09/388,260

[22] Filed: Sep. 1, 1999

[51] Int. Cl.⁷ .................................................. A61K 31/437
[52] U.S. Cl. ............................................................. 514/293
[58] Field of Search ............................................. 514/293

[56] References Cited

PUBLICATIONS

Susan E. Piscopo, "The Complexities of Sarcoid Tumors", Sep. 1999, *Equine Practice*, vol. 21, No. 8.
M. Wyman et al., "Immunotherapy in Equine Sarcoid" a Report of Two Cases, J.Am.Vet.Med. Assn., vol. 171, pp. 449–451, 1977.
J. Baker, "Equine Sarcoids", The Veterinary Record, vol. 102, No. 8, pp. 179–180, 1978.
M. Robinson, "Equine Sarcoids", The Veterinary Record, vol. 102, No. 11, p. 248, 1978.
E. Marti et al., "Report of the First International Workshop on Equine Sarcoids", Equine Veterinary Journal, vol. 25, pp. 397–407, 1993.
3M Pharmaceuticals Press Release, "3M Pharmaceuticals Gets Clearance To Market Aldara™ (Imiquimod)", 1977.
U. Studer et al, "Treatment of Equine Sarcoid With an Unspecific Immunostimulants", Schwetz. Arch. Tierheck vol. 139, pp. 385–391, 1997.
3M Pharmaceuticals Press Release, "Patient–Applied Aldara™ Found Effective For Genital Warts", 1998.
T. Winston et al., "Treatment of Equine Sarcoins", J. Am. Vet. Med. Assn., vol. 175, p. 775, 1979.
K. Beultner et al., Abstract of "Treatment of Genitar Warts With an Immune–Response Modifier (Imiquimod)," J. Am. Acad. DGRM, 38(2), 1998.
3M Pharmaceuticals Press Release, Patient–Applied Description Cream Offers Effective Alternative to Ablade 1998.
L. Goodrich et al., "Equine Sarcoids", Equine Practice, vol. 14, pp. 607–623, 1988.

*Primary Examiner*—Phyllis G. Spivack
*Attorney, Agent, or Firm*—Flangan & Flangan; John K. Flanagan; John R. Flanagan

[57] ABSTRACT

A method for the treatment of topical sarcoidosis on equine includes providing a therapeutic substance substantially in the form of an imiquimod 5% cream and applying the therapeutic substance a plurality of times spaced at intervals from one another to an outer surface of the body of an equine such that the therapeutic substance substantially covers symptomatic manifestations of topical sarcoidosis on the outer surface of the equine body.

20 Claims, No Drawings

METHOD EMPLOYING IMIQUIMOD CREAM FOR TREATMENT OF TOPICAL SARCOIDOSIS ON EQUINE

BACKGROUND OF THE INVENTION

1. Field of the Invention

The present invention generally relates to topical sarcoidosis and, more particularly, is concerned with a method employing an imiquimod cream for the treatment of topical sarcoidosis on equine.

2. Description of the Prior Art

Sarcoidosis is an ailment of equine, such as horses, donkeys and mules. Sarcoidosis is most commonly topical in nature. Sarcoids are the typical symptomatic manifestations of sarcoidosis. Sarcoids are tumors which are non-metastatic. Sarcoids are formed by proliferation of neoplastic fibroblasts which results in the thickening or ulceration of skin. Sarcoids may occur alone or in clusters. Sarcoids commonly arise on the head, limbs and abdomen, but can occur anywhere on the body of a horse. Sarcoids are the most frequently found tumor of horses. Though not life threatening, sarcoids generally reduce the value of a horse because their location on the horse adversely affects the performance of the horse when employed for various activities. Sarcoidosis is believed to be caused by infection of the bovine papilloma virus.

A variety of treatments for topical sarcoidosis have been tried over the years, including surgical excision, cryotherapy, immunotherapy, radiotherapy, laser therapy, hyperthermia and topical and intratumoral chemotherapy. Surgical excision involves the use of surgical techniques to cut and remove sarcoids from adjacent healthy tissue. Cryotherapy involves freezing sarcoids. A refrigerant, commonly liquid nitrogen, is sprayed on the sarcoids to kill the cells of the tumors. Immunotherapy involves the use of antigens to stimulate lymphocytes and to increase natural killer cells of the host animal to kill the cells of the sarcoids. An attenuated strain of Mycobacterium bovis is commonly used in this procedure. Radiotherapy involves the use of radiation to kill the cells of the sarcoids. Radioactive isotopes are used to deliver a continuous and high dose of radiation locally to each tumor without affecting adjacent healthy tissue. Laser therapy involves cutting and evaporating sarcoids with a laser. Carbon dioxide lasers are commonly used for this procedure. Hyperthermia involves heating the tumor cells to kill them. The hyperthermia is commonly induced by a radio-frequency current. Topical chemotherapy involves topical applications of caustic or antimetabolite drugs to kill sarcoid cells. Podophyllum and 5-fluorouracil are commonly used for this procedure. Intratumoral chemotherapy involves the use of implants of caustic or antimetabolite drugs within the sarcoids to kill the cells of the tumors. Cisplatin and 5-fluorouracil are commonly used in the implants.

Each of these prior art methods of treatment for topical sarcoidosis appears to be somewhat satisfactory to varying degrees. However, many of the treatments have adverse side effects or risks, none of the treatments are universally effective in eliminating or reducing sarcoids and new sarcoids frequently recur following each of the treatments and additional treatments are required. Thus, a need remains for a more effective solution in treating topical sarcoidosis on equine without introducing any new problems in place of the aforementioned problems of the prior art treatments.

Imiquimod cream has been used to treat ailments of humans. Imiquimod is an immune-response modifier which is capable of inducing cytokines, including interferon alfa, tumor necrosis factor-a and interleukins 1, 6 and 8. An imiquimod 5% cream, developed by 3M Pharmaceuticals of St. Paul, Minn., and manufactured and marketed under the trademark "Aldara," has been used to treat genital warts of humans. Unlike sarcoids, genital warts are primarily sexually transmitted and caused by the human papilloma virus and the warts of this human disease are found only in the genital and perianal areas of females and males.

As sarcoids of equine and genital warts of humans are normally transmitted by different means, are caused by different viruses, occur most frequently on different parts of the body and are found on different animal species, it does not appear that any significant relation exists between these two ailments. Although the 3M Pharmaceuticals imiquimod 5% cream was reported to have been tested on laboratory animals and that it demonstrated antiviral, antitumor and adjuvant activity, heretofore it has not been applied to equine nor was it developed to treat any equine disease.

SUMMARY OF THE INVENTION

The present invention provides a method for the treatment of topical sarcoidosis on equine which is designed to satisfy the aforementioned need. The equine sarcoidosis treatment method of the present invention employs an imiquimod cream. The imiquimod cream is applied several times topically to sarcoids on equine. The imiquimod cream clears the sarcoids. Scarring and hair loss are avoided in most cases. The sarcoids do not recur after the treatments.

Accordingly, the present invention is directed to a method for the treatment of topical sarcoidosis on equine. The method of the present invention comprises the steps of: (a) providing a therapeutic substance comprised of a therapeutically effective amount of an imiquimod; and (b) applying the therapeutic substance at least once to an outer surface of a body of an equine such that the therapeutic substance at least partially covers symptomatic manifestations of topical sarcoidosis on the outer surface of the body of the equine.

More particularly, the providing step of the method includes providing the therapeutic substance substantially in the form of a cream, such as in the form of an imiquimod 5% cream. The applying step includes applying the therapeutic substance to the outer surface of the body of the equine such that the therapeutic substance substantially covers symptomatic manifestations of topical sarcoidosis on the outer surface of the body of the equine. The therapeutic substance is applied a plurality of times to the outer surface of the body of the equine. The applying step further includes applying the therapeutic substance a first time to the outer surface of the body of the equine and then a second time to the outer surface of the body of the equine after the first time. The applying step further includes applying the therapeutic substance the second time 5 to 7 days after the first time. The applying step also includes applying the therapeutic substance a third time to the outer surface of the body of the equine after the second time. The applying step further includes applying the therapeutic substance the third time 3 to 4 weeks after the second time. The applying step also includes applying the therapeutic substance one to three more times to the outer surface of the body of the equine after the third time. The applying step further includes applying the therapeutic substance the one to three more times 3 to 4 weeks after the third time and 3 to 4 weeks after one another.

These and other features and advantages of the present invention will become apparent to those skilled in the art upon a reading of the following detailed description.

DETAILED DESCRIPTION OF THE INVENTION

The present invention is directed to a method for the treatment of topical sarcoidosis on equine. The equine sarcoidosis treatment method of the present invention basically includes the steps of providing a therapeutic substance comprised of a therapeutically effective amount of an imiquimod and applying the therapeutic substance at least once to an outer surface of a body of an equine, such as a horse, such that the therapeutic substance at least partially covers symptomatic manifestations of topical sarcoidosis on the outer surface of the body of the equine. The outer surface of the equine body may include any location where sarcoids, the symptomatic manifestations of topical sarcoidosis, occur on the equine. The sarcoids are tumors which are commonly in the form of lesions.

To describe the present invention in greater detail, the equine sarcoidosis treatment method further includes providing the therapeutic substance substantially in the form of a cream and, more particularly, in the form of an imiquimod 5% cream. The inventor herein is the first person to experiment with and, totally unexpectedly and coming as a complete surprise to persons of ordinary skill in the art who regularly have treated equine sarcoidosis with the traditional methods described earlier, find that the imiquimod 5% cream developed by 3M Pharmaceuticals of St. Paul, Minn. for treatment of genital warts of humans, and manufactured and marketed under the trademark "Aldara", is a therapeutic substance having a therapeutically effective amount of imiquimod for treatment of equine sarcoidosis when carried out in accordance with the method of the present invention. The therapeutic substance is preferably applied to the outer surface of the body of the equine such that the therapeutic substance substantially or entirely covers symptomatic manifestations of topical sarcoidosis on the outer surface of the equine body.

It is most often necessary to apply the therapeutic substance a plurality of times to the outer surface of the equine body, though the method need not be so limited. The therapeutic substance is generally applied a first time to the outer surface of the equine body, a second time to the outer surface of the equine body after the first time and, again, a third time to the outer surface of the equine body after the second time. A preferred interval between the first and second times should be 5 to 7 days, though the interval need not be so limited. A preferred interval between the second and third times should be 3 to 4 weeks, though the interval need not be so limited.

It may also be necessary to apply the therapeutic substance one to three more times to the outer surface of the equine body after the third time. The preferred interval between the third time and the next time should be 3 to 4 weeks and between each of the one to three more times should likewise be 3 to 4 weeks, though the interval need not be so limited. It is believed by the inventor herein of the equine sarcoidosis treatment method of the present invention that the therapeutic substance should not be applied more than six times on individual sarcoids if no positive effect has occurred by then, as additional applications over six are not likely to result in positive results if the first six applications did not have any positive effect. If no positive response occurs after six applications, the inventor herein would deem the treatment a failure. It is notable, however, that the inventor has not had any such failures.

To demonstrate the efficacy of the equine sarcoidosis treatment method of the present invention, the inventor herein has treated approximately thirty (30) sarcoids in horses of various breeds. Some of the horses had no prior treatment before receiving treatment by the method of the present invention. Most of the horses, however, had received standard treatments, such as one of the treatments mentioned above in the background of the invention or other treatments, which were not effective. All of the horses treated by the method of the present invention were diagnosed with a sarcoid by a biopsy or were clinically diagnosed by a veterinarian. In each treatment with the method of the present invention, the clinical cure was determined by resolution (disappearance) of the sarcoid with normal skin and hair regrowth in its place. In some cases, a second biopsy was done to confirm the resolution of the sarcoid. Swelling, oozing and crusting of the treated areas were considered a clinical sign of the method of the present invention having a positive therapeutic effect.

A first study subject was an eight year old Irish draft gelding which had sarcoids on the chest and jaw. The sarcoids were of the flat and verrucous types. The sarcoids were initially treated with floristan, topical steroids and zinc oxide icthymol without relief. The sarcoids were then treated with three applications of the imiquimod 5% cream by the method of the present invention with the result being total clearing of all lesions, no scarring, total hair regrowth and no recurrence.

A second study subject was a seven year old Thoroughbred gelding which had verrucous type sarcoids over the left brow and subcutaneous type sarcoids on the right rear flank. The sarcoids were initially treated with cryosurgery with recurrence two times. The verrucous type sarcoids were then treated with three applications of the imiquimod 5% cream and the subcutaneous type sarcoids were then treated with five applications of the imiquimod 5% cream by the method of the present invention with the result being total clearing of all lesions, no scarring, total hair regrowth and no recurrence.

A third study subject was a nine year old Thoroughbred gelding which had sarcoids. The sarcoids were initially treated with Hilton Ditton for four months without relief. The sarcoids were then treated with three applications of the imiquimod 5% cream by the method of the present invention with the result being total clearing of all lesions, total hair regrowth and no recurrence. A slight scar remained without hair regrowth in the area of the lesions, but all scarring had accrued from the sarcoids prior to the treatment by the method of the present invention.

A fourth study subject was an eight year old Thoroughbred gelding which had flat to verrucous sarcoids. The sarcoids were initially treated with 5-fluorouracil intralesionally with partial clearing and then recurrence. The sarcoids were then treated with three applications of the imiquimod 5% cream by the method of the present invention with the result being total clearing of all lesions, no scarring, total hair regrowth and no recurrence.

A fifth study subject was a seven year old Pony of America gelding which had verrucous type sarcoids on the sheath. The sarcoids were initially treated with cryosurgery with recurrence and then with BCG after recurrence without relief. The sarcoids were then treated with three applications of the imiquimod 5% cream by the method of the present invention with the result being total clearing of all lesions, no scarring and no recurrence, though hair regrowth did not occur on the sheath.

A sixth study subject was a six year old Conemara pony gelding which had nodular sarcoids. The sarcoids received no prior art treatment. The sarcoids were treated with five applications of the imiquimod 5% cream by the method of the present invention with the result being total clearing of all lesions, no scarring, total hair regrowth and no recurrence.

A seventh study subject was a five year old Thoroughbred mare which had verrucous type sarcoids on the inner posterior thigh. The sarcoids received no prior art treatment. The sarcoids were treated with three applications of the imiquimod 5% cream by the method of the present invention with the result being total clearing of all lesions, no scarring and no recurrence, though hair regrowth did not occur on the inner thigh.

An eighth study subject was a seven year old Thoroughbred gelding which had verrucous type sarcoids on the left side of the neck. The sarcoids received no prior art treatment. The sarcoids were treated with three applications of the imiquimod 5% cream by the method of the present invention with the result being total clearing of all lesions, no scarring, total hair regrowth and no recurrence.

A ninth study subject was a twenty year old saddle bred Arabian which had verrucous type sarcoids on the chest and neck. The sarcoids were initially treated with 5-fluorouracil without relief. The sarcoids were then treated with four applications of the imiquimod 5% cream by the method of the present invention with the result being total clearing of all lesions, no scarring, total hair regrowth and no recurrence.

A tenth study subject was a six year old Thoroughbred gelding which had flat sarcoids on the inner hind legs. The sarcoids received no prior art treatment. The sarcoids were treated with three applications of the imiquimod 5% cream by the method of the present invention with the result being total clearing of all lesions, no scarring, total hair regrowth and no recurrence.

Additional study subjects included a Warmblood, a Clydesdale, a Saddlebred, two Quarterhorses and an Arab. These horses had sarcoids on either the canthus, eye, one or more legs, neck or inguinal area. The sarcoids were treated with two to six applications of the imiquimod 5% cream by the method of the present invention with the results being successful resolution in all but two cases where only partial resolution occurred.

It is thought that the present invention and its advantages will be understood from the foregoing description and it will be apparent that various changes may be made thereto without departing from the spirit and scope of the invention or sacrificing all of its material advantages, the form hereinbefore described being merely a preferred or exemplary embodiment thereof.

I claim:

1. A method for the treatment of topical sarcoidosis on equine, comprising the steps of:
   (a) providing a therapeutic substance comprising a therapeutically effective amount of imiquimod; and
   (b) applying the therapeutic substance at least once to an outer surface of the body of an equine such that the therapeutic substance at least partially covers symptomatic manifestations of topical sarcoidosis on the outer surface of the equine body.

2. The method of claim 1 wherein the providing step includes providing the therapeutic substance substantially in the form of a cream.

3. The method of claim 1 wherein the providing step includes providing the therapeutic substance substantially in the form of an imiquimod 5% cream.

4. The method of claim 1 wherein the applying step includes applying the therapeutic substance to the outer surface of the equine body such that the therapeutic substance substantially covers symptomatic manifestations of topical sarcoidosis on the outer surface of the equine body.

5. A method for the treatment of topical sarcoidosis on equine, comprising the steps of:
   (a) providing a therapeutic substance comprising a therapeutically effective amount of imiquimod; and
   (b) applying the therapeutic substance a plurality of times to an outer surface of the body of an equine such that the therapeutic substance at least partially covers symptomatic manifestations of topical sarcoidosis on the outer surface of the equine body.

6. The method of claim 5 wherein the providing step includes providing the therapeutic substance substantially in the form of a cream.

7. The method of claim 5 wherein the providing step includes providing the therapeutic substance substantially in the form of an imiquimod 5% cream.

8. The method of claim 5 wherein the applying step includes applying the therapeutic substance to the outer surface of the equine body such that the therapeutic substance substantially covers symptomatic manifestations of topical sarcoidosis on the outer surface of the equine body.

9. The method of claim 5 wherein the applying step includes applying the therapeutic substance a first time to the outer surface of the equine body and then a second time to the outer surface of the equine body after the first time.

10. The method of claim 9 wherein the applying step includes applying the therapeutic substance the second time 5 to 7 days after the first time.

11. The method of claim 9 wherein the applying step includes applying the therapeutic substance a third time to the outer surface of the equine body after the second time.

12. The method of claim 11 wherein the applying step includes applying the therapeutic substance the third time 3 to 4 weeks after the second time.

13. The method of claim 11 wherein the applying step includes applying the therapeutic substance one to three more times to the outer surface of the equine body after the third time.

14. The method of claim 13 wherein the applying step includes applying the therapeutic substance the one to three more times 3 to 4 weeks after the third time and 3 to 4 weeks after one another.

15. A method for the treatment of topical sarcoidosis on equine, comprising the steps of:
   (a) providing a therapeutic substance substantially in the form of an imiquimod 5% cream; and
   (b) applying the therapeutic substance a plurality of times to an outer surface of the body of an equine such that the therapeutic substance substantially covers symptomatic manifestations of topical sarcoidosis on the outer surface of the equine body.

16. The method of claim 15 wherein the applying step includes applying the therapeutic substance a first time to the outer surface of the equine body and then a second time to the outer surface of the equine body after the first time.

17. The method of claim 16 wherein the applying step includes applying the therapeutic substance the second time 5 to 7 days after the first time.

18. The method of claim 16 wherein the applying step includes applying the therapeutic substance a third time to the outer surface of the equine body after the second time.

19. The method of claim 18 wherein the applying step includes applying the therapeutic substance the third time 3 to 4 weeks after the second time.

20. The method of claim 18 wherein the applying step includes applying the therapeutic substance one to three more times to the outer surface of the equine body after the third time.

* * * * *